United States Patent [19]  [11]  4,198,350
Fields  [45]  Apr. 15, 1980

[54] AMINATION/DEMETHYLATION PROCESS
[75] Inventor: Ellis K. Fields, River Forest, Ill.
[73] Assignee: Standard Oil Company (Indiana), Chicago, Ill.
[21] Appl. No.: 657,498
[22] Filed: Feb. 12, 1976

Related U.S. Application Data

[60] Continuation-in-part of Ser. No. 107,544, Jan. 18, 1971, abandoned, which is a division of Ser. No. 663,245, Aug. 25, 1967, Pat. No. 3,625,989.

[51] Int. Cl.$^2$ ............................................. C07C 85/11
[52] U.S. Cl. ..................................... 260/580; 549/68; 260/347.3; 260/347.4; 260/347.7; 260/689; 546/311
[58] Field of Search ................................ 260/580, 689

[56] References Cited

U.S. PATENT DOCUMENTS

| | | | |
|---|---|---|---|
| 2,377,071 | 5/1945 | Castner et al. | 260/580 |
| 3,293,295 | 12/1966 | Swakon et al. | 260/580 X |
| 3,504,035 | 3/1970 | Polinski et al. | 260/580 |

OTHER PUBLICATIONS

Fields et al., "J. Amer. Chem. Soc.", vol. 89:13, pp. 3224–3228 (1967).

Janzen, "J. Amer. Chem. Soc.", vol. 87:15, pp. 3531–3532 (1965).

*Primary Examiner*—John Doll
*Attorney, Agent, or Firm*—William C. Clarke; William T. McClain; Arthur G. Gilkes

[57] ABSTRACT

This invention relates to the intramolecular oxidation and reduction of aromatic hydrocarbons containing at least one methyl group and a nitro group ortho to the methyl group. Further, it relates to preparing methyl o-amino arylcarboxylates and aromatic amines. The process comprises reacting aromatic hydrocarbons having at least one methyl group and a nitro group ortho to the methyl group in a solvent at a temperature of about 450° to 750° C. When the solvent is methanol, methyl o-amino arylcarboxylates useful in anesthetics, printing inks for polyethylene, and useful in the manufacture of azo dyes are produced. Novel substituted methyl anthranilates have been produced which have the foregoing uses. When no solvent is used or the solvent is benzene, cyclohexane, toluene, hexafluorobenzene or any other non-reactive solvent, the compounds are demethylated and aromatic amines are produced. These aromatic amines are useful as pesticides, anti-oxidants and as pickling inhibitors for aluminum and zinc and as curing agents for epoxy resins.

13 Claims, No Drawings

AMINATION/DEMETHYLATION PROCESS

This application is a continuation-in-part of application Ser. No. 107,544 filed Jan. 18, 1971 now abandoned, which was a divisional application of Ser. No. 663,245 filed Aug. 25, 1967 now U.S. Pat. No. 3,625,989.

This invention relates to the intramolecular oxidation and reduction of aromatic hydrocarbons containing at least one methyl group and a nitro group ortho to the methyl group. When the reaction is conducted in an inert or non-reactive solvent such as benzene, cyclohexane, hexafluorobenzene, or toluene, the methyl group on the methyl o-nitro aromatic hydrocarbons is oxidized and decarboxylation takes place while the nitro group is reduced to the amino group. When methanol is used as a solvent, methyl o-amino arylcarboxylates are produced. In these compounds the nitro group is reduced to the amino group but the methyl group is oxidized to the carboxylate group which is esterified by the methanol.

This invention further relates to a process for the preparation of methyl o-amino arylcarboxylates and aromatic amines. Novel methyl methyl o-amino arylcarboxylates are prepared by reacting aromatic hydrocarbons having at least one methyl group and a nitro group ortho to the methyl group in methanol at a temperature of about 450° to 750° C.

The process of this invention is a novel one-step process. Prior to the instant invention the method for preparing methylo-amino arylcarboxylates such as methyl anthranilates consisted of three separate steps from o-nitrotoluene or substituted o-nitrotoluene. These steps include oxidation of nitrotoluene to the o-nitrobenzoic acid. This processing step demands expensive and relatively slow oxidizing agents such as potassium permanganate or chromic acid. Air oxidation has not succeeded with o-nitrotoluenes. The second step consisted of the reduction of o-nitrobenzoic acid by hydrogenation or with iron and in acid to the o-amino benzoic acid. The third step consisted of esterification with methanol in an acid catalyst to give the methyl anthranilates.

By contrast the one-step process of this invention consists of heating the aromatic hydrocarbons containing at least one methyl group and a nitro group ortho to the methyl group such as o-nitrotoluene in methanol at a temperature of about 450° to 750° C. to give methyl anthranilates. A further advantage of my process is that ring methyl- and polymethyl methyl anthranilates which could not be prepared even by the prior art three-step process described above because oxidation in the first step would readily oxidize all the methyl group are easily synthesized as shown by the reaction of nitro-p-xylene and 5-nitropseudocumene in methanol. Thus, my novel process can readily produce 3-methyl anthranilates which could not be prepared by the process known in the prior art. For example, novel methyl anthranilates of the following formula have been prepared:

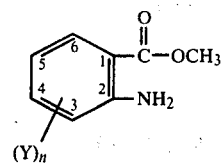

wherein Y is one of the following: fluorine, chlorine or monovalent methyl radical, and n is an integer of 1. Also the reduction in the second step of the conventional synthesis of methyl anthranilates can often reduce or hydrogenolyze out halo or other reactive groups. This danger is not involved in the process of this invention.

Furthermore, my process is useful in preparing aromatic amines from aromatic hydrocarbons containing at least one methyl group and a nitro group ortho to the methyl group when the reaction is conducted without a solvent or in the presence of a non-reactive solvent including benzene, cyclohexane, toluene, or hexafluorobenzene at a temperature of about 450° to 750° C. for 1 to 100 seconds.

Prior to the instant invention, the hydrogen necessary to reduce the nitro group to an amine group was provided by hydrogen gas in the presence of a suitable catalyst or by an aliphatic or cyclic hydrocarbon which had readily available hydrogen. The use of molecular hydrogen in presence of a suitable catalyst such as metallic copper, iron, gold, silver, nickel, platinum, among others are well-known. Castner et al, U.S. Pat. No. 2,377,071, teaches the reduction of mononitro compounds to amines with hydrogen provided by aliphatic or cyclic hydrocarbon compounds preferably in the presence of a highly active catalyst. Castner also teaches that the mononitro compounds must be sufficiently stable to allow reaction without decomposition of the nitro compound at the reaction temperature, i.e., below 450° C., while the aliphatic and cyclic hydrocarbons react to produce carbon monoxide and carbon dioxide.

Castner teaches that a variety of hydrocarbons, including cyclohexane, may be used as a source of hydrogen. In the instant invention, I have found that cyclohexane is an inert solvent, the methyl group ortho to the nitro group being a preferred hydrogen donor to the nitro group, the presence or absence of cyclohexane or other hydrocarbons being immaterial to the invented process. In the presence of two methyl groups, both ortho to a single nitro group on the ring, only one of the two methyl groups acts as a hydrogen donor. The other methyl group remains on the ring.

The decomposition of nitrobenzene alone at 600° C. in the presence of Vycor chips, as is taught by E. F. Fields et al, J.O.A.C.S., Vol. 89, No. 13, pages 3224–3228 (1967), yields a small percentage of aniline, a 1.4% relative concentration of a 30 wt.% yield, which can only be through the abstraction of hydrogen from another molecule of nitrobenzene but this is, however, only a minor reaction. The major products from the thermal decomposition of nitrobenzene in the presence of Vycor chips are benzene, phenol, biphenyl, biphenyl derivatives, terphenyls and quaterphenyls, accounting for 83.6% of the decomposition products. The presence of Vycor chips in Fields et al, as above, is an integral portion of the report of the thermal decomposition of nitrobenzene.

My process is useful in preparing methyl o-amino carboxylate and aromatic amines as shown from the following reaction:

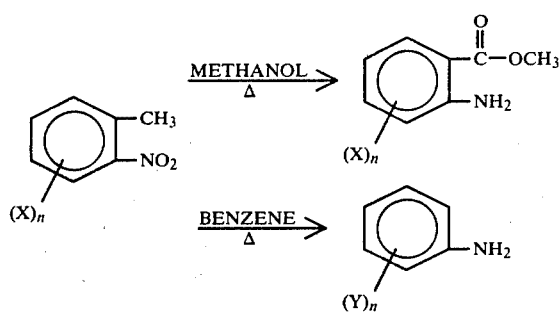

wherein X or Y is hydrogen or chlorine, bromine, alkoxy, carbomethoxy, and alkyl radical such as methyl or aryl radical, such as benzene, toluene, xylene or mixtures of these, and n is an integer from 1–4.

Further, polynuclear hydrocarbons such as biphenyl, naphthalene, anthracene, phenanthrene, pyrene, rubrene, chrysene and terphenyl, containing at least one methyl group and a nitro group ortho to the methyl group are converted in methanol at about 450° to about 750° C. to methyl o-amino arylcarboxylates, or to polynuclear amines without a solvent or when the solvent is inert such as benzene, cyclohexane, toluene or hexafluorobenzene, as shown for 2-methyl-1-nitro naphthalene in the following equation:

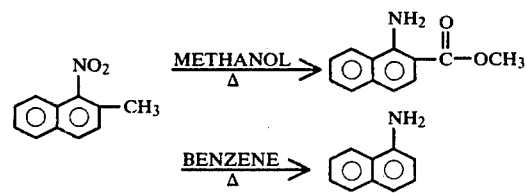

In general the process is carried out by reacting the aromatic hydrocarbon containing at least one methyl group and a nitro group ortho to the methyl group in methanol at a temperature of about 450° to 750° C. The mole ratio of the o-nitrotoluene moiety containing aromatic compound to methanol can be 1:1 to about 1:20 and the mole ratio to inert solvent such as benzene, cyclohexane, toluene or hexafluorobenzene, can be 1:1 to 1:40, and the contact time of 1–100 seconds can be used. Under the preferred condition the mole ratio of the o-nitrotoluene to methanol is 1:5 to 1:10 and the ratio of o-nitrotoluene moiety-containing aromatic compound to benzene, cyclohexane, toluene or hexafluorobenzene can be 1:1 to 1:40. The preferred temperature is 500° to 600° C. and the preferred contact time is 5–25 seconds. The reaction is conducted under an inert atmosphere. Nitrogen, helium or carbon dioxide are the preferred inert gases. In the preferred embodiment one mole of o-nitrotoluene is reacted in 10 moles of methanol, at a temperature of about 600° C. for about 6–8 seconds. The resulting methyl anthranilate is obtained as a residue after the methanol is distilled off. The product of my invention is useful in the manufacture of azo dyes, in printing inks for ethylene polymers and anesthetics.

Use of Vycor chips can provide an auxiliary means of reaction temperature control but use of Vycor chips is not an essential element of the process. Any means of reaction temperature control such as an inert packing of glass or ceramic beads is suitable. The process operates equally well irrespective of the composition of the reactor walls or presence of Vycor chips as no evidence has been found of the presence or need of a contact catalyst. The reactor walls can be quartz, stainless steel, or any non-reactive material.

It is an essential element of my invention that a methyl group be in an ortho position to the nitro group of the aromatic compound. In the presence of more than one ortho methyl group, only one methyl group is demethylated. While I do not wish to be bound by any theory concerning the mechanism of the process for preparing aromatic amines in the absence of a reactive solvent, it is theorized that the process occurs by the simultaneous intramolecular oxidative and reductive demethylation of a single ortho methyl group and the nitro group to convert the nitro group to an amine group while simultaneously oxidizing the methyl group to a carboxyl group and then decarboxylating the intermediate carboxyl group. It is theorized that in the presence of methanol or any other reactive solvent, the intermediate carboxyl group reacts. In the presence of methanol or other suitable alcohol, the carboxylate group is esterified by the methanol or other alcohol. It is further theorized that in the absence of a solvent which does not react with the intermediate carboxyl group, the process continues to the demethylation of the methyl group from the aromatic hydrocarbon compound. Inasmuch as the process is solely a thermal (i.e., no catalyst is required) process which is theorized as operating by the simultaneous intramolecular oxidative and reductive demethylation of the methyl group and o-nitro group, the process is a general process which takes place irrespective of other groups upon the aromatic ring. These other intramolecular groups can be hydrogen, chlorine, bromine, alkoxy, carbomethoxy, and alkyl radicals in number from one to six.

For purposes of this invention, the term "aromatic compound" is defined as an organic compound containing a carbocyclic or heterocyclic nucleus whether or not it is condensed with other rings with points of attachment on separate adjoining carbon atoms for the nitro and methyl radicals, the heterocyclic ring containing at least one hetero atom selected from the group consisting of nitrogen, oxygen and sulfur. When the hetero atom is oxygen or sulfur, the aromatic heterocyclic nucleus is a five-membered ring containing two conjugated double bonds with points of attachment for two radicals other than the nitro and methyl radicals. When the hetero atom is nitrogen, the aromatic heterocyclic nucleus is a six-membered ring containing three conjugated double bonds with points of attachment for three radicals other than the nitro and methyl radicals. The aromatic carbocyclic compound contains a benzene nucleus and is selected from the group consisting of monocyclic and polycyclic hydrocarbons of benzene and fused benzene rings. One to six ring hydrogens of the heterocyclic nucleus and the carbocyclic nucleus can be replaced with radicals selected from the group consisting of chlorine, bromine, alkoxy, carbomethoxy, methyl, benzene, toluene and xylene radicals and mixtures of these. The term "benzene nucleus" denotes the presence of a six-membered ring all of whose members are carbons and containing three conjugated double bonds. The said polycyclic hydrocarbons are defined as being selected from the group consisting of biphenyl, naphthalene, anthracene, phenanthrene, pyrene, rubrene, chrysene and terphenyl hydrocarbons. The term "aromatic amine" is defined as denoting an aromatic compound which contains an amine group directly attached to a carbon atom of the cyclic nucleus. A ring hydrogen is attached to a carbon atom of the cyclic nucleus. The term "demethylate" is defined as denoting the removal of a methyl group by oxidation of the methyl group, followed by decarboxylation of the intermediate carboxyl group, and the substitution of an alternate radical or atom which can be a hydrogen atom.

In summary, the process of my invention relates to a process for preparing aromatic amines and methyl o-amino arylcarboxylates. The process comprises heating an aromatic compound having at least one nitro group and a methyl group ortho to the nitro group at a temperature of from about 450° to 750° C. for 1 to 100 seconds.

When methanol or another suitable reactive alcohol is utilized as a solvent, the intermediate carboxyl group is esterified by the methanol or other alcohol. When the solvent is methanol, methyl o-amino arylcarboxylates are produced. When the said process is carried out in the absence of a solvent or if said solvent comprises a solvent which is non-reactive with the intermediate carboxyl group, an aromatic amine is produced, the said ortho methyl group being demethylated. Preferred non-reactive solvents are benzene, cycylohexane and hexafluorobenzene. The presence of a non-reactive solvent is not essential as the process occurs in a solvent-less condition.

In an alternative embodiment of the process of my invention, it may be run by adding 70–100% nitric acid, 0.5–5 moles, at 15°–30° C. to a stirred solution of 1 mole toluene in 2–20 moles benzene and contacting for 10 seconds to 30 minutes; pumping this nitration mixture from the nitration reaction into the Vycor tube at 500°–600° C. with contact times of 5–30 seconds; withdrawing the solution of aniline in benzene thus produced, and distilling to recover the benzene and to obtain the aniline. Similarly, substituted toluenes having one or both ortho positions free may be nitrated and converted to the substituted aniline.

The following examples further illustrate my invention. Examples are given of the process with and without the use of Vycor chips, Vycor and quartz tubes, and with and without the presence of solvents. Analyses and identification of products were by retention times and area % compared to authentic samples in gas chromatographic columns containing polyethylene glycol sebacate on Chromosorb W, as well as by low voltage (7.5 e.v. uncorrected) mass spectra in a Consolidated Model 21-103c mass spectrometer, with the inlet system at 250° or 325° C., and with the repellers maintained at an average potential of 3 volts. In addition, for analysis and identification, use was made of a directly coupled gas chromatograph mass spectrometer combination also employing a 21-103c instrument with an electron multiplier in place of the Faraday-cup detector. This type of analytical tool has been described by R. S. Gohlke, Anal. Chem. 31, 535(1959); J. P. Lindeman and J. L. Annis, ibid., 32, 1742(1960); J. T. Watson and K. Biemann, ibid., 36, 1135(1964).

EXAMPLE I

A solution of 6.14 ml. (0.05 mole) o-nitrotoluene in 20.5 ml. (0.5 mole) methanol was passed through a Vycor tube containing Vycor chips at 600° C. under nitrogen flowing at 0.1 cu. ft./hr. Contact time was 7.2 seconds. The condensed product was distilled to recover 17 ml. methanol and give a residue of 3.45 g. containing 1.615 g. of methyl anthranilate; yield, 21.4 mole %.

EXAMPLE II

The same quantities of o-nitrotoluene and methanol were reacted as in Example I, except the temperature was 500° C. and the contact time was 7.9 seconds. The condensate was distilled to recover 16 ml. methanol and leave a residue of 3.75 g., which analyzed 26.9% o-nitrotoluene and 36% methyl anthranilate. The yield of methyl anthranilate was 19.4%.

EXAMPLE III

A solution of 8.58 g. (0.05 mole) 4-chloro-2-nitrotoluene in 20.5 ml. (0.5 mole) methanol was passed into the Vycor tube at 600° C. under nitrogen at 0.1 cu.ft./hr.; contact time was 10.6 seconds. Distillation gave 17 ml. of methanol and 3.5 g. product that contained 3.348 g. of methyl 4-chloroanthranilate. The yield was 36 mole %.

EXAMPLE IV

A solution of 7.76 g. (0.05 mole) 4-fluoro-2-nitrotoluene in 20.5 ml. (0.5 mole) methanol was passed into the Vycor tube at 600° C. under nitrogen at 0.1 cu.ft./hr.; contact time was 11.3 seconds. Distillation recovered 17 ml. methanol and left 3.2 g. product that contained 1.785 g. of methyl 4-fluoroanthranilate. The yield was 21 mole %.

EXAMPLE V

A solution of 7.56 g. nitro-p-xylene (0.05 mole) in 20.5 ml. (0.5 mole) methanol was passed into the Vycor tube at 600° C. under nitrogen at 0.1 c.ft./hr.; contact time was 10 seconds. Distillation gave 17 ml. methanol and 3.8 g. product that contained 2.06 g. of methyl-4-methyl anthranilate. The yield was 25 mole %.

EXAMPLE VI

A solution of 8.2 g. (0.05 mole) 5-nitropseudocumene in 20.5 ml. (0.5 mole) methanol was passed into the Vycor tube at 600° C. under nitrogen at 0.1 cu.ft./hr.; contact time was 13 seconds. Distillation gave 16 ml. methanol and 4.0 g. product that contained 1.79 g. of methyl 3,4-dimethyl anthranilate. The yield was 20 mole %.

EXAMPLE VII

Methyl-3-nitro-4-methyl benzoate was prepared from p-toluic acid according to H. King and W. O. Murch, J. Chem. Soc. (London), 127, 2639 (1925). A solution of 9.75 g. (0.05 mole) of this ester in 20.5 ml. (0.5 mole) methanol was passed into the Vycor tube at 600° C. under nitrogen flowing at 0.1 cu.ft./hr.; contact time was 6.8 seconds. Distillation gave 17 ml. methanol and 3.7 g. product, that contained 0.681 g. of dimethyl-3-amino terephthalate (6 mole %) and 2.797 g. of methyl anthranilate (37 mole %).

EXAMPLE VIII

A solution of 9.36 g. (0.05 mole) 2-methyl-1-nitronaphthalene in 20.5 ml. (0.5 mole) methanol was passed into the Vycor tube at 600° C. under nitrogen at 0.1 cu.ft./hr.; contact time was 10 seconds. Distillation gave 13 ml. methanol and 4.8 g. product that contained 0.9955 g. of methyl-1-amino-2-naphthoate. The yield was 11%.

Examples of the wide utility of the methyl anthranilates of my invention include:

The manufacture of azo dyes, U.S. Pat. No. 2,774,755; Ger. No. 955,858.
As a perfume ingredient, Jap. No. 1831; Ger. No. 927,946.
In printing inks for ethylene polymers, Ger. No. 1,024,531.
For absorbing ultraviolet light in cellulose ester film, Dutch No. 87,528.
As anesthetics. M. Häring, Helv. Chim. Acta. 43, 104 (1960).

EXAMPLE IX

A solution of 6.14 ml. (0.05 mole) o-nitrotoluene in 8.88 ml. (0.1 mole) benzene was passed through a Vycor tube containing Vycor chips under nitrogen flowing at 0.1 cu.ft./hr. at 600° C. Contact time was 16.3 seconds. The condensate was distilled to recover 6.1 ml. benzene and give a residue of 5.3 g., of which 2.654 g. was aniline. The yield of aniline was 57%.

EXAMPLE X

A mixture of 6.14 ml. (0.05 mole) o-nitrotoluene and 10.8 ml. (0.1 mole) cyclohexane was passed through a Vycor tube containing Vycor chips at 600° C. under nitrogen flowing at 0.1 cu.ft./hr. Contact time was 16.2 seconds. The condensate was distilled to recover 2 ml. cyclohexane and obtain 3.3 g. of residue, of which 1.63 g. was aniline. The yield of aniline was 35%.

EXAMPLE XI

A mixture of 7.56 g. (0.05 mole) nitro p-xylene and 17.76 ml. (0.2 mole) benzene was passed through a Vycor tube containing Vycor chips at 600° C. under nitrogen flowing at 0.1 cu.ft./hr. Contact time was 18.5 seconds. The condensate was distilled to recover 14 ml. benzene and obtain 5.35 g. of residue, of which 3.24 g. was m-toluidine. The yield of m-toluidine was 59%.

EXAMPLE XII

A mixture of 8.58 g. (0.05 mole) 4-chloro-2-nitrotoluene and 17.76 ml. benzene (0.2 mole) was passed into a Vycor tube containing Vycor chips at 600° C. under nitrogen flowing at 0.1 cu.ft./hr. Contact time was 20.1 seconds. The condensate was distilled to recover 12 ml. benzene and obtain 2.5 g. residue, of which 0.962 g. was m-chloroaniline. The yield of m-chloroaniline was 15%.

EXAMPLE XIII

A mixture of 8.2 g. (0.05 mole) 5-nitropseudocumene and 17.17 ml. (0.2 mole) benzene was passed into a Vycor tube containing Vycor chips at 600° C. under nitrogen flowing at 0.1 cu.ft./hr. Contact time was 20.3 seconds. The condensate was distilled to recover 15 ml. benzene and obtain 4.55 g. residue, of which 1.14 g. was 4-amino-o-xylene. The yield of 4-amino-o-xylene was 19%.

EXAMPLE XIV

A mixture of 9.75 g. (0.05 mole) methyl 3-nitro-4-methyl benzoate and 17.76 ml. (0.2 mole) benzene was passed into a Vycor tube containing Vycor chips at 600° C. under nitrogen flowing at 0.1 cu.ft./hr. Contact time was 28.5 seconds. The condensate was distilled to recover 13. ml. benzene and obtain 6.0 g. residue, of which 2.4 g. was methyl-3-aminobenzoate. The yield of methyl 3-aminobenzoate was 32%.

EXAMPLE XV

A mixture of 9.36 g. (0.05 mole) 2-methyl-1-nitronaphthalene and 17.76 ml. (0.2 mole) benzene was passed into a Vycor tube containing Vycor chips at 600° C. under nitrogen flowing at 0.1 cu.ft./hr. Contact time was 21.6 seconds. The condensate was distilled to recover 15 ml. benzene and obtain 5.1 g. residue which was almost pure 1-naphthylamine. The yield was 70%.

The aromatic amines produced by my invention are useful as dye intermediates, antioxidants, pesticides, extractants for hydrocarbons, pickling inhibitors for alumina and zinc, and curing agents for epoxy resins, among others. These are but a few of the many patents dealing with the utility of the aromatic amines produced by my invention:

U.S. Pat. Nos. 2,801,979; 2,952,717
Ger. Pat. Nos. 889,488; 894,888; 1,019,083
Fr. Pat. Nos. 1,004,169; 1,020,456
Swiss Pat. No. 293,893

EXAMPLE XVI

This example illustrates the production of aniline from ortho nitrotoluene in a non-reactive solvent, hexafluorobenzene.

2.74 grams (0.02 m moles) of ortho nitrotoluene dissolved in 18.6 grams (0.10 m moles) of hexafluorobenzene were passed through a Vycor tube containing Vycor chips at 600° C. under nitrogen flowing at 500 cc/minute. Contact time was 20 seconds. The condensed gases were distilled to recover 18.2 grams of hexafluorobenzene and a residue that contained 1.0 gram of aniline. The yield was 52 mole %. Analysis was by gas chromatography.

EXAMPLE XVII

This example illustrates the production of aniline from ortho nitrotoluene in an empty Vycor tube.

6.14 Ml (0.05 mole) ortho nitrotoluene dissolved in 8.88 ml. (0.1 mole) benzene was passed through an empty Vycor tube under nitrogen flowing at 0.1 cubic ft/hr at 600° C. Contact time was 16.5 seconds. The condensate was distilled to recover 6.2 ml of benzene and give a residue of 5.26 grams of which 2.70 grams was aniline. The yield of aniline was 57.6%. Analysis was by gas chromatography.

EXAMPLE XVIII

This example illustrates the lack of any catalytic effect upon the process caused by the Vycor wall of the Vycor tube or caused by decomposition products building up upon the Vycor wall in the thermal reaction of ortho nitrotoluene to give aniline.

Three successive charges of 6.14 ml (0.05 mole) of ortho nitrotoluene in 8.88 ml (0.1 mole) of benzene were passed through the same Vycor tube under the same conditions as in Example XVII. Yields of aniline were 57.5%, 57.8% and 57.3% respectively. There was hence no evidence of a catalytic effect by deposits upon the reaction.

The same charge of ortho nitrotoluene in benzene as above was passed through an empty quartz tube under the same conditions as above. The yield of aniline was 57.2%.

EXAMPLE XIX

This example illustrates the production of aniline from ortho nitrotoluene in cyclohexane.

6.14 Ml (0.05 mole) ortho nitrotoluene in 10.8 ml (0.1 mole) cyclohexane was passed through an empty Vycor tube at 600° C. under nitrogen flowing at 0.1 cubic ft/hour. Contact time was 16.2 seconds. The condensate was distilled to recover 2.2 ml of cyclohexane and 3.5 grams residue of which 1.60 grams were aniline. The yield of aniline was 36.4%.

EXAMPLE XX

This example illustrates the production of an aromatic aniline containing an alkyl radical.

7.56 Grams (0.05 mole) nitro-paraxylene in 17.76 ml. (0.2 mole) benzene was passed through an empty Vycor tube at 600° C. under nitrogen flowing at 0.1 cubic feet/hour. Contact time was 18.5 seconds. The condensate was distilled to recover 15 ml of benzene and obtain 3.21 grams metatoluidine. Yield was 58.5% of metatoluidine.

EXAMPLE XXI

This example illustrates the production of an aromatic amine containing a polynuclear hydrocarbon radical. 9.36 Grams (0.05 mole) 2-methyl-1-nitronaphthalene in 17.17 ml. (0.2 mole) benzene were passed through an empty Vycor tube at 600° C. under nitrogen flowing at 0.1 cubic feet/hour. Contact time was 20 seconds. The condensate was distilled to recover 15.4 ml of benzene and 4.96 grams of 1-naphthylamine. The yield was 68%.

What is claimed is:

1. A process for preparing aromatic amines which comprises heating a composition consisting essentially of an aromatic compound having a nitro group and a methyl group ortho to each other at a temperature of from about 450° C. to 750° C. for 1-100 seconds to convert simultaneously said nitro group to an amine group and demethylate said ortho methyl group wherein any solvent present is selected from the group consisting of benzene and hexafluorobenzene.

2. The process of claim 1 wherein the said process consists essentially of heating said aromatic compound at said temperature for said 1-100 seconds.

3. The process of claim 1 wherein the said solvent is benzene.

4. The process of claim 1 wherein the said solvent is hexafluorobenzene.

5. The process of claim 1 wherein the said aromatic compound containing at least one nitro group and a methyl group ortho to the nitro group is selected from the group consisting of monocyclic and polycyclic hydrocarbons of benzene and fused benzene rings, the said polycyclic hydrocarbons being selected from the group consisting of biphenyl, naphthalene, anthracene, phenanthrene, pyrene, rubrene, chrysene, and terphenyl hydrocarbons.

6. The process of claim 5 wherein one to six ring hydrogens of said monocyclic and polycyclic hydrocarbons are replaced with radicals selected from the group consisting of chlorine, bromine, alkoxy, carbomethoxy, methyl, benzene, toluene, xylene radicals and mixtures of these.

7. The process of claim 1 wherein the said aromatic compound containing at least one nitro group and a methyl group ortho to the nitro group comprises a heterocyclic compound wherein the hetero atoms are selected from the group consisting of nitrogen, oxygen and sulfur atoms and points of attachment of said nitro and methyl groups are on separate adjoining carbon atoms.

8. The process of claim 7 wherein one to six ring hydrogens of the said heterocyclic compound are replaced with radicals selected from the group consisting of chlorine, bromine, alkoxy, carbomethoxy, methyl, benzene, toluene, xylene radicals and mixtures of these.

9. The process of claim 1 wherein the aromatic compound containing one nitro group and a methyl group ortho to the nitro group is 5nitropseudocumene.

10. The process of claim 1 wherein the aromatic compound containing one nitro group and a methyl group ortho to the nitro group is 2-methyl-1-nitronaphthalene.

11. The process of claim 1 wherein the aromatic compound containing one nitro group and a methyl group ortho to the nitro group is ortho nitrotoluene.

12. The process of claim 1 wherein the aromatic compound containing one nitro group and a methyl group ortho to the nitro group is nitro-p-xylene.

13. The process of claim 1 wherein the aromatic compound containing one nitro group and a methyl group ortho to the nitro group is 4-chloro-2-nitrotoluene.

* * * * *

UNITED STATES PATENT OFFICE
CERTIFICATE OF CORRECTION

Patent No. 4,198,350          Dated April 15, 1980

Inventor(s) Ellis K. Fields

It is certified that error appears in the above-identified patent and that said Letters Patent are hereby corrected as shown below:

| Patent Column | Line | |
|---|---|---|
| 1 | 28 | "methyl methyl" should be --methyl-- |
| 1 | 36 | "methylo-amino" should be --methyl o-amino-- |
| 10 | 35 | "5nitropseudocumene" should be --5-nitropseudocumene-- |

Signed and Sealed this

Twenty-second Day of July 1980

[SEAL]

Attest:

SIDNEY A. DIAMOND

*Attesting Officer*      *Commissioner of Patents and Trademarks*